(12) United States Patent
Rembrand

(10) Patent No.: US 10,856,781 B2
(45) Date of Patent: Dec. 8, 2020

(54) METHOD AND A DEVICE FOR MONITORING A HUMAN BRAIN'S SUB-COGNITIVE ACTIVITY USING OTO-ACOUSTIC EMISSIONS

(71) Applicant: SensPD Ltd., Kiryat Tivon (IL)

(72) Inventor: Raphael Rembrand, Kiryat Tivon (IL)

(73) Assignee: SensPD Ltd., Basmat Tab'un (IL)

( * ) Notice: Subject to any disclaimer, the term of this patent is extended or adjusted under 35 U.S.C. 154(b) by 288 days.

(21) Appl. No.: 14/902,853

(22) PCT Filed: Sep. 17, 2013

(86) PCT No.: PCT/IL2013/000072
§ 371 (c)(1),
(2) Date: Jan. 5, 2016

(87) PCT Pub. No.: WO2015/004648
PCT Pub. Date: Jan. 15, 2015

(65) Prior Publication Data
US 2016/0183849 A1 Jun. 30, 2016

Related U.S. Application Data

(60) Provisional application No. 61/843,931, filed on Jul. 9, 2013.

(51) Int. Cl.
| | |
|---|---|
| *A61B 5/12* | (2006.01) |
| *A61B 5/00* | (2006.01) |
| *A61B 7/02* | (2006.01) |
| *A61B 7/04* | (2006.01) |
| *H04R 1/10* | (2006.01) |

(52) U.S. Cl.
CPC .............. *A61B 5/12* (2013.01); *A61B 5/4064* (2013.01); *A61B 5/6817* (2013.01);
(Continued)

(58) Field of Classification Search
CPC ........... A61B 5/12; A61B 5/16; A61B 5/4064; A61B 5/6817; A61B 5/7246; A61B 5/7278; A61B 7/023; A61B 7/04
(Continued)

(56) References Cited

U.S. PATENT DOCUMENTS

| | | | | |
|---|---|---|---|---|
| 4,374,526 A | | 2/1983 | Kemp | |
| 5,372,142 A | * | 12/1994 | Madsen | .................... A61B 5/12 600/552 |

(Continued)

OTHER PUBLICATIONS

Alex (Sandy) Pentland, Honest Signals, by: The MIT Press: London, 2008 | ISBN: 9780262162562. A quotation in the book by Prof. Pentland.

(Continued)

*Primary Examiner* — Daniel L Cerioni
(74) *Attorney, Agent, or Firm* — Smith, Gambrell & Russell, LLP

(57) ABSTRACT

The present invention relates to a method for monitoring the brain's sub-cognitive activity through otoacoustic emissions. More specifically, the present invention deals with a method and device for monitoring the brain's functions that are manifested by sub-cognitive activities. The sub cognitive activities are monitored by matching to the spectrograms of a standard evoked oto-acoustic emissions signals to monitor mismatches as indicators of normal or malfunctioning sub cognitive neurological functions. The invention relates also to a device for monitoring the brain's sub-cognitive activity through otoacoustic emissions. More specifically, the present invention deals with a method and device for monitoring the brain's functions that are manifested by sub-cognitive activities. The sub cognitive activities are monitored by matching to the spectrograms of a standard evoked oto-acoustic emissions signals to monitor mismatches as indi- (Continued)

cators of normal or malfunctioning sub cognitive neurological functions.

5 Claims, 2 Drawing Sheets

(52) U.S. Cl.
CPC .......... *A61B 5/7246* (2013.01); *A61B 5/7278* (2013.01); *A61B 7/023* (2013.01); *A61B 7/04* (2013.01); *A61B 2562/222* (2013.01); *H04R 1/1016* (2013.01)

(58) Field of Classification Search
USPC ........................................................ 600/559
See application file for complete search history.

(56) References Cited

U.S. PATENT DOCUMENTS

| 6,149,605 | A | 11/2000 | Christiansen | |
|---|---|---|---|---|
| 2012/0197153 | A1* | 8/2012 | Kraus | A61B 5/04845 600/545 |

OTHER PUBLICATIONS

D.T. Kemp: "Stimulated acoustic emissions from within the human auditory system" published in J. Acoust. Soc. Am. 1978;64(5):1386-91.

Hear ID Auditory Screening and Diagnostic System. Web-sites: http://www.mimosaacoustics.com/pdf/HearID_5_Datasheet.pdf and , http://www.mimosaacoustics.com/pdf/HearID_5_DP_Datasheet.pdf.

Gammaitoni L, Hänggi P, Jung P, Marchesani F., Stochastic resonance, published in: Rev. Mod. Phys. 1998;70(1):223-87.

Eduardo Lugo, Rafael Doti, Jocelyn Faubert , Ubiquitous Cross modal Stochastic Resonance in Humans: Auditory Noise Facilitates Tactile, Visual and Proprioceptive Sensations. Published in: PLoS ONE (www.plosone.org) Aug. 2008, vol. 3 Issue 8.

Feng FG, Martino KM, Linthicum FH, Soli SD. Auditory perception in vestibular neurectomy subjects. Hear Res. 2000;142(12): 10212.

Courschesne E. chapter in Schopler E, Mesibov GB, editors. Neurobiological issues in autism. New York: Plenum. p. 285-324. Cited as: Courchesne, E., Lincoln, A.J., Yeung-Courchesne, R. et al. J Autism Dev Disord (1989) 19: 1. doi:10.1007/BF02212714.

Katz, Jack. Neuroscience and Biobehavioral Reviews 36 (2012) 836-854.

Katz, Jack (1992). "Classification of auditory processing disorders". In Jack Katz and Nancy Austin Stecker and Donald Henderson. Central auditory processing: a transdisciplinary view. St. Louis: Mosby Year Book. pp. 81-92. ISBN 978-1-55664-372-9.

O'Connor K (Dec. 2011). "Auditory processing in autism spectrum disorder: A review". Neurosci Biobehav Rev 36 (2): 836-54. doi:10. 1016/j.neubiorev.2011.11.008. PMID 22155284.

\* cited by examiner

METHOD AND A DEVICE FOR MONITORING A HUMAN BRAIN'S SUB-COGNITIVE ACTIVITY USING OTO-ACOUSTIC EMISSIONS

FIELD OF THE INVENTION

The present invention relates to a method and a device for monitoring the brain's sub-cognitive activity through otoacoustic emissions. More specifically, the present invention deals with a method and device for monitoring sensory related brain functions that are manifested by sub-cognitive activities. The sub cognitive activities are monitored by comparing to the spectrograms of a standard evoked oto-acoustic emissions signals to monitor for mismatches as indicators for normal or malfunctioning sub cognitive neurological functions.

BACKGROUND OF THE INVENTION

Brain activity encompasses a huge number of functions: cognitive, sensory, motor and many others. The present invention refers to monitoring a class of functions that are sub-cognitive or sub-liminal brain functions that are sub-consciously operated and affect human communications.

Human communication is based on "formal" and "informal" exchange of mutually recognized information-signals such as, but not limited to, the display of body movements, typically referred to as "body language" and the production of audio sounds. The terms "audio sounds" and "audio signals" are used interchangeably from herein A great deal of exchanged information-signals is conveyed by unintentional, "informal-signals".

The term "informal communication" implies that there is a bi-directional "give and take" as one person focuses on the other while the other senses the approval or rejection by the first person. Informal communication exchange is typically carried out without the persons involved being consciously aware of it. In his book: Honest Signals, by: Alex (Sandy) Pentland, The MIT Press: London, 2008|ISBN: 9780262162562, Prof. Pentland points out that some of the information-signals are difficult to fake, thus, they are perceived as being trustworthy. An example of such a trust worthy interaction signal is manifested by the expression "Look me in the eyes".

The exchange of audio information-signals by humans is typically, but not exclusively, referred to as talking or conversing. Conversing requires the emitting of audio sounds by a human speaker and the reception of the audio sounds by a human "responding side". In continuing the conversation, the "responding side" (the side spoken to) comprehends the audio signals and responds by producing audio sounds in a manner that is received and comprehended by the speaker. In talking, humans sub-consciously analyze how active they are within a conversation (in terms of the amplitude and frequency of speech and a person's gestures). By applying the same analysis to audio responses, the levels of mutual interest, empathy and interest shown by the "responding side" can be deduced; this activity is sometimes referred to as: "reading between the lines".

A "responding side" conducting a conversation in an environment which has significant background sounds, typically but not limited to, other talking sounds or music sounds not meant for him, is able to "filter out" and comprehend the audible signals of the speaker. The "responding side" is able to comprehend the audio signals of the speaker even in the presence of fairly loud background sounds by focusing his attention on the speaker. This focusing action is both cognitive and sub-cognitive, thus, the manner of the reply-actions of the "responding side" includes both conscientious and sub-conscientious activities.

The ability to hear and comprehend audio-signals over back ground sounds, is referred from herein as: Speech in Background Babble Discrimination (SIBD) or, interchangeably, "the cocktail party effect". SIBD is elaborated in: Rembrand, R., Tetin-Schneider, S. 2012 International Tinnitus Journal, 17(1) pp. 8-15. As explained later in this text, this discrimination mechanism is an example of a sub-cognitive activity of the brain.

In an article by D. T. Kemp: "Stimulated acoustic emissions from within the human auditory system" published in J. Acoust. Soc. Am. 1978; 64(5):1386-91 the structure and functioning mechanism of the human ear is explained. In a normal human ear, referred from herein interchangeably as the "hearing system" and the "auditory system", ambient sound causes the tympanic membrane (i.e., the eardrum) to vibrate. The ossicular chain (i.e., malleus, incus and stapes) which is located between the tympanic membrane and the oval window mechanically transmits these vibrations to the fluid within the cochlea, which in turn generates a traveling wave in the fluid. These waves cause the inner hair cells which are part of Corti's organ, to vibrate; thereby causing the auditory neurons connected to these inner hair cells to fire and convey sensory information respective of the ambient sound, to the brain stem. The Corti's organ also includes a plurality of Outer Hair Cells (OHC). The cranial olivary nucleus which is part of the brain-stem transmits an electric signal respective of the detected ambient sound, to the cell membrane of the outer hair cells, via a nerve bundle known as the Olivo-Cochlear tract. The electric signal causes the outer hair cells to vibrate. This mechanism reinforces the vibrations produced in the inner hair cells and improves the detection of sound by the brain. The stochastic signal produced by the outer hair cells is referred to in the art as "Oto-Acoustic Emissions (OAE)" and whose amplitude in a normal subject amounts to several tens of decibels.

Systems for measuring OAE are known in the art. These systems generate transient sound and apply it to the ear canal of a subject as a stimulus. After the stimulus sound is stopped, the evoked OAE corresponding to the stimulus sound is recorded. Given below are two US patents based on measuring OAE in tested subjects.

U.S. Pat. No. 4,374,526 (Kemp): "Hearing Faculty Testing and Apparatus Thereof" describes a testing apparatus for obtaining medical information on the state of an examined ear using an improved audio-metric test that does not require the active participation of the subject examined. The hearing faculty test and apparatus therefore is based on the finding that sound input to the ear gives rise to a returned wave from and related to the condition of the inner ear, this wave being detectable as an echo from the ear drum.

U.S. Pat. No. 6,149,605 (Christiansen): "Oto-acoustic emission analyzer" describes a hand-held, battery-driven, apparatus utilized for measuring the hearing ability of an examined person.

U.S. Pat. No. 4,374,526 (Kemp) and U.S. Pat. No. 6,149, 605 refer to measuring OAE as a mean to evaluate the physiological and hearing conditions of the inner ear of an examined subject. The applied technique in each subject examined includes steps of applying an audio signal (stimulus) to the ear of the subject, detecting the audio waves (OAE) returning from the inner ear, and processing the signal respective of the detected wave form. The audio signal applied to the ear is short (<2 ms). The detection of the echoes is performed according to a time gating scheme. The technique in each patent is based on recording the produced echo after the stimulus and the immediate response (allowing for a latency of at least 3 ms) thereto (i.e., the response of the ear to the stimulus sound such as echo), are over. The processing involves averaging sequence of such recordings. Existing devices include a stimulus generator with an electro-acoustic transducer (earphone) to sound it, a microphone to record the response and a processor to control the operation, interface the user and analyze the results. In addition, they may include an additional earphone for two tones and an additional microphone recording ambient sounds to allow for removing external noises.

The purpose of existing OAE measurement devices is to analyze the performance of the inner ear in general and the functioning of the Outer Hair Cells (OHC) in particular. For medical physiological analysis of the ear, current devices require a "clean" OAE response from the ear. The devices typically emit detectable short audio signals that start at a range of about 500 Hz and is repeated for 0.25-20 seconds. The response sounds from the ear are detected immediately after the stimulus subsides. Examples of OAE medical hearing analysis devices are provided in web-sites of the Mimosa Acoustics Company from Illinois, USA: Hear ID Auditory Screening and Diagnostic System (web-site: http://www.mimosaacoustics.com/pdf/HearID_5_Datasheet.pdf and http://www.mimosaacoustics.com/pdf/HearID_5_DP_Datasheet.pdf.

Stochastic Rresonance (SR) is a mathematical theory derived from chaos theory. SR is required in order to understand how the audio signals generated by the OHC assist in the SIBD process. In a review paper by Gammaitoni L, Hanggi P, Jung P, Marchesoni F. entitled: Stochastic resonance, published in: Rev. Mod. Phys. 1998; 70(1):223-87, SR is explained as follows: For the SR transformation to occur, two conditions must be met: An energetic activation barrier or, more generally, a form of threshold (e.g. the nerve's sensitivity threshold) and a weak coherent input (such as a periodic signal e.g. a vowel). When these conditions are met and a source of stochastic noise (e.g. OAE) is added to the coherent input, the response of the system undergoes resonance-like behavior as a function of the noise level; hence the name Stochastic Resonance. The combined signals are non-linearly spread and shifted to higher frequency allowing for easier sensory input discrimination. The listener has a sense of "sharpening" of the sounds he/she hears.

The OAE response to complex stimuli—Speech Evoked Oto-Acoustic emissions (SEOAE) signal is the brain's way of assisting in the focus and discrimination task of our senses. The stochastic signal generated by the outer hair cells of the inner ear is nature's way of utilizing Stochastic Resonance (SR) transformation for this task.

Rembrand R. and Tetin-Schneider S. in their article from 2012 (quoted above), report that the spectral analyses of OAE show that it matches quite closely the spectrum of speech shaped noise. Their tests show that OAE plays a key role in "Speech in Noise Discrimination"—hearing and understanding talking over back ground sounds. The discrimination task is using the stochastic signal generated by the OHC as a pre-filtering mechanism.

Another way of explaining the way SR works is as follows: An implementation of any filtering system requires some a-priori knowledge of the desired output of the system. The human hearing system does not have a-priori knowledge of the sound-signals that will be processed to obtain a desired output electrical signals, thus, a sound-signals "pre-filtering" is required. The process of "pre-filtering" in the hearing system is adding "designated" stochastic noise to the input signal and by the transformation of stochastic resonance.

The present invention provides a method and a device that uses the OAE response to monitor the performance of the pre-filtering system that controls the OHC. The OAE system acts as a pre-filtering system when a complex signal with frequency contents of speech is fed to the auditory system throughout the entire testing period. Alternatively, or simultaneously, ambient sounds, "collected" from the surrounding, can be fed to the auditory system. The method and the device of the present invention include monitoring the OAE signal that is generated internally in the auditory system. In order to monitor the OAE the external signals need to be subtracted from the total signal output. The subtraction is accomplished by utilizing a Signal Processor (SP). The OAE signal after subtraction of the activation signal is referred from herein as the "pure OAE signal".

"Brain Waves" is a manner of speech that refers to the electric potential activity in the brain and is the result of localized ion pumping that affect neighboring locations. The ion pumping causes an electrical-signal that travels through synapses, axons and nerve cells. The electric potential generated by single neuron is far too small to be picked up directly therefore standard measurements such as Electroencephalography (EEG), thus, EEG measurements reflect the summation of the synchronous activity of thousands or millions of neurons. EEG measurements are not easily performed since the patient needs to be cooperative (or sedated) and many electrodes need to be placed externally and in some types of measurements, even inserted into the brain. Pure OAE signal recordings offer a way to circumvent this difficulty. Since OHC activity is controlled by the brain nerve system and more specifically, through the Olivo-Cochlear nerve bundle, monitoring the OHC outputs (pure OAE) enables indirect monitoring of the brain waves in the vicinity of the inner ear.

Humans are mostly aware of the brain's cognitive activity sensory or motor functions. Most cognitive functions are supported by sub-cognitive activities. For example: when a hand moves to grab an object we are mostly aware of the "end product" the object is grabbed. In the process of moving the hand towards an object a complex hand-eye coordination process occurs. The hand-eye coordination process activates many muscles that contract/release and the sense of touch allows for application of just the right amount of force to handle the object. Sub-cognitive activities reside in the grey zone between cognitive—full awareness and control e.g. speech—and non-cognitive—e.g. intestinal smooth muscles contractions. Breathing and the mode of breathing for example are usually automatic but we can resume control of it either cognitively or indirectly through our state of mind (as in states of excitement or stress).

In order to discriminate between multi-talker babble and target speech the human brain uses the OAE system. The brain initiates, through the OHC, a general speech shaped OAE stochastic signal and 3-5 ms later the brain subconsciously generates OAE that optimizes the discrimination process of the target talker. The fitness of the preferred frequencies generated by the OHC as predicted by the SR transformation for the audio signals of the speaker are indicative of the listener's attention focus and the intensity and quality of the connection between the communicating parties. Clinical tests reported by Rembrand and Tetin-Schneider (in the article previously quoted) support the above statement.

Research findings have shown that there is a "cross modal effect" between the senses. The "cross modal effect" indicates that in hearing certain stochastic auditory noises the stochastic resonance (SR) transformation causes the enhancement of the tactile sense and the perception of visual signals of the listener (reference: Ubiquitous Crossmodal Stochastic Resonance in Humans: Auditory Noise Facilitates Tactile, Visual and Proprioceptive Sensations By; Eduardo Lugo, Rafael Doti, Jocelyn Faubert. Published in: PLoS ONE (www.plosone.org) August 2008, Vol. 3 Issue 8). By measuring the pure OAE signals of a person observing a gallery of pictures is becomes possible to quantitatively indicate which of the pictures most attracted his attention.

Research findings have shown that people deprived of the ability to sub-cognitively control their OAE output signals (due to neurectomy of efferents of the olivo-cochlear nerve in their ears) have reduced speech in background babble discrimination (SIBD) and suffer from vocal attention shift delays (reference: Zeng F G, Martino K M, Linthicum F H, Soli S D. Auditory perception in vestibular neurectomy subjects. Hear Res. 2000; 142(12): 10212).

Other research findings have shown that people with the symptoms of autism have significant vocal attention shift delays. Courschesne E. in an article from 1987: A neurophysiological view of autism (reference: Schopler E, Mesibov G B, editors. Neurobiological issues in autism. New York: Plenum. p. 285-324) states: " . . . we found that people with autism have limited ability to sub-cognitively generate appropriate OAE signals and this inability to generate appropriate OAE signals causes people with autism to have limited ability to interpret complex (e.g. speech) signals".

The term "central auditory processing disorder (CAPD) is a described by the American Academy of Audiology (website: http://www.audiology.org/resources/documentlibrary/Documents/CAPD%20Guidelines%208-2010.pdf)) in its publication from August 2010: "Diagnosis, Treatment and Management of Children and Adults with Central Auditory Processing Disorder" as an umbrella term for a variety of disorders that affect the way the brain processes auditory information. Typically, people with CAPD have no evidence of neurological disease and the diagnosis is made on the basis of performance on behavioral auditory tests. Auditory processing is "what we do with what we hear". In CAPD there is a mismatch between peripheral hearing ability (which is typically normal) and ability to interpret or discriminate sounds. CAPD include, but is not limited to, the disorders of: autism and dyslexia. References: 1) Katz, Jack (1992). "Classification of auditory processing disorders". In Jack Katz and Nancy Austin Stecker and Donald Henderson. Central auditory processing: a transdisciplinary view. St. Louis: Mosby Year Book. pp. 81-92. ISBN 978-1-55664-372-9. O'Connor K (December 2011). "Auditory processing in autism spectrum disorder: A review". Neurosci Biobehav Rev 36 (2): 836-54. doi:10.1016/j.neubiorev.2011.11.008. PMID 22155284.

The monitoring of pure OAE signals, in accordance with the present invention, yields quantitative information about informal interactions.

By setting a standard of pure OAE signals typically found in people classified as "normal" and/or "regular", and comparing the standard to pure signals obtained from tested individuals, it is possible to quantify and characterize the informal interaction formed between the examined person and the people and/or items he or she is in contact with. By comparing standards of pure OAE signals from people classified as "normal" and/or "regular" to pure OAE signals of individuals with behavioral difficulties, it is possible to audibly quantify and characterize the lack of formation of informal interactions with the surrounding and to quantify the neurological malfunctioning of such individuals.

SUMMARY OF THE INVENTION

The device of the present invention monitors the sub-cognitive activity of a human brain using oto-acoustic emissions evoked in a human ear. The device is composed of at least one earphone, at least one microphone and a signal processor. The earphone(s) and microphone are positioned in a probe that comes into close contact with the ear of the monitored subject and the probe is in contact with the signal processor. In deployment of the device, the earphone emits audio signals to the ear and the microphone picks up the audio signals and evoked oto-acoustic emissions signals from said ear and transmits the signals to the signal processor, The signal processor subtracts the earphone emitted audio signals from the evoked oto-acoustic emissions signals and produces a set of signal spectrograms, The evoked oto-acoustic emissions signal spectrograms are compared to the spectrograms of a standard evoked oto-acoustic emissions signals to monitor for mismatches as indicators of normal or malfunctioning sub cognitive neurological functions.

The present invention presents a method for monitoring the sub-cognitive activity of a human brain using evoked oto-acoustic emissions in a human ear, The method deploys audio signals emitted to an ear that evoke oto-acoustic emissions response signal in the ear. A a-signal processor subtracts the emitted audio signals from the evoked oto-acoustic emissions signal and produces a set of oto-acoustic emissions signal spectrograms, The spectrograms are compared to standard set of spectrograms to monitor for mismatches as indicators of normal or malfunctioning sub cognitive neurological functions.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

DETAILED DESCRIPTION OF EMBODIMENTS

Figure 1:
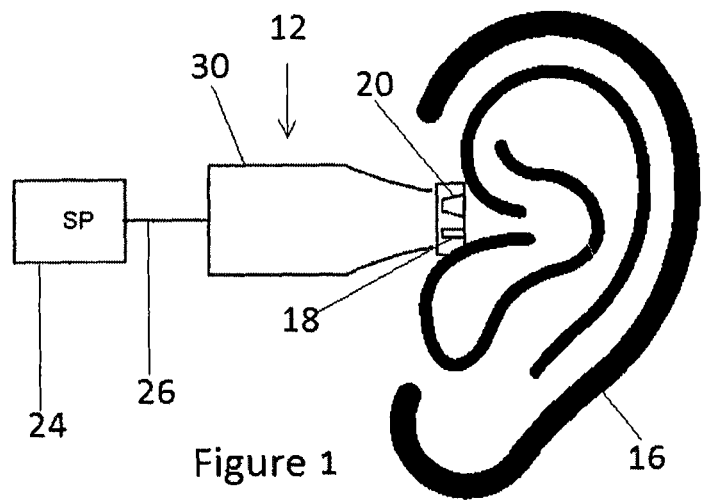
FIG. 1 is a schematic display of an embodiment of an ear's response monitoring device in accordance with present invention that includes: a microphone that captures the ear's response, an earphone that emits stimulus sounds and a signal processor device.

Typically the inner ear responds to two types of stimuli: controlled—generated by an earphone and uncontrolled— which includes any sound that might reach the ear, e.g. ambient noise, that the device of the present invention has no control of. Embodiments of a OAE monitoring device in accordance with the present invention include the components: at least one earphone for emitting generated audio signals, at least one microphone for picking up the inner ear's response (in the form of the OAE) and a Signal Processor (SP). The emitted audio signals by the earphone are pre-recorded audio sounds of human speech and or other sound tracks of stimulating sounds. The earphone and microphones are positioned together in a probe that comes into close contact with the ear. Optionally, another microphone (or microphones) is connected to the SP and is not positioned in the probe. The probe can contain the SP or be connected, either by wire or by a wireless-connection to the SP. The SP is communicates (by wire or wirelessly) with the microphone and the earphone. The generated signals from the earphone and the evoked OAE response signals of the ear are subtracted and the resultant signals, defined as pure AOE signals, are analyzed to generate a 3D spectrogram, In case of a second microphone, the combined signal from the earphone generated signal picked up by the probe-positioned microphone and the signals picked up by the second microphone (not probe-positioned) are subtracted by the SP from the evoked OAE response of the ear. The pure OAE signal is either further processed in the probe by a built-in computer-processor (closely connected to the SP, not shown in the figures) and transmitted to a computerized storage and read-out device such as a screen or a printer (not shown) or, alternatively, the SP-data is transmitted to a computer processor (not shown in the figures) and is processed and analyzed in accordance with the purpose of the OAE monitoring that were preformed. The connection between the SP and the storage or processor computer can be either by wire or by a wireless-connection.

In deploying the device of the present invention, the pure OAE signal obtained from a monitored person, when the person is exposed to a standard stimulating signal or a measured ambient sound means (after signals subtraction, as explained above) is analyzed for the deviation from standard responses appropriate for that given situation. The intensity and quality of the communication-focus of the listener to a potential communicating party in a "real event" talk (or sense enhancement, in case of "cross modal effect" between the senses) is quantified by the results of this monitoring.

Another deployment of the device of the present invention is quantitatively monitoring of persons suspected of having CAPD by exposing a person to a variety of standard stimulating audio signals. The presence of CAPD is determined by the magnitude of deviations from the norm as explained in the previous paragraph.

Figure 2:
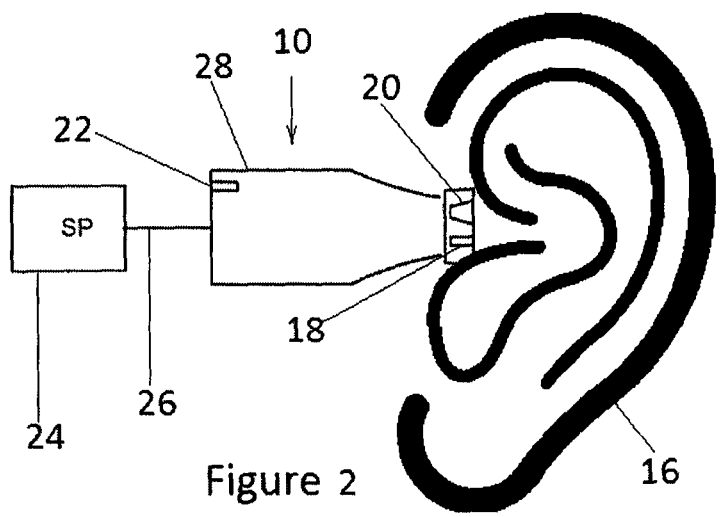
FIG. 2 is a schematic display of an embodiment of an ear's response monitoring device in accordance with present invention that includes: a microphone that captures the ear's response, an earphone that emits stimulus sounds, a second microphone that captures ambient sounds that eventually reach the ear and a signal processor device.

Reference is now made to two embodiments of the device in accordance with present invention shown in FIGS. 1 and 2

FIG. 1 is a schematic display of an embodiment of an inner ear's OAE response monitoring device (12) in accordance with present invention. The embodiment includes: a microphone (18) that captures the ear's OAE response, an earphone (20) that emits stimulus sounds and a SP device (24). The microphone (18) and earphone (20) are positioned in a probe (30). The connection between probe (30) and SP (24) is designated (26). Probe (30), when deployed, is in close vicinity or in contact with the ear (16). The use of embodiment (12) is limited to sound controlled environments such as a laboratory or a clinic.

FIG. 2 is a schematic display of another embodiment of an ear's OAE emission response monitoring device (10) in accordance with present invention. Embodiment (10) uses both ambient sounds and generated sounds through an earphone. Embodiment (10) includes: a microphone (18) that captures the ear's OAE emission response, a microphone (22) that captures ambient sounds that eventually reach the ear, an earphone (20) that that emits generated sounds and a SP device (24). Microphone (18) and microphone (22) and earphone (20) are connected to probe (28). The connection between probe (28) and SP (24) is designated (26). Probe (28), when deployed, is in close vicinity or in contact with the ear (16).

In the OAE the monitoring devices described in the embodiments, the earphone and the microphone(s) components are embedded in a probe which is in contact with a SP processor. The microphones and earphone have frequency response extending (at least) between 40 Hz and 12 kHz. Man machine interface is handled by the processor. Further processing of the results can be handled by the processor itself or by communicating the monitored data to a host computer.

Figure 3:
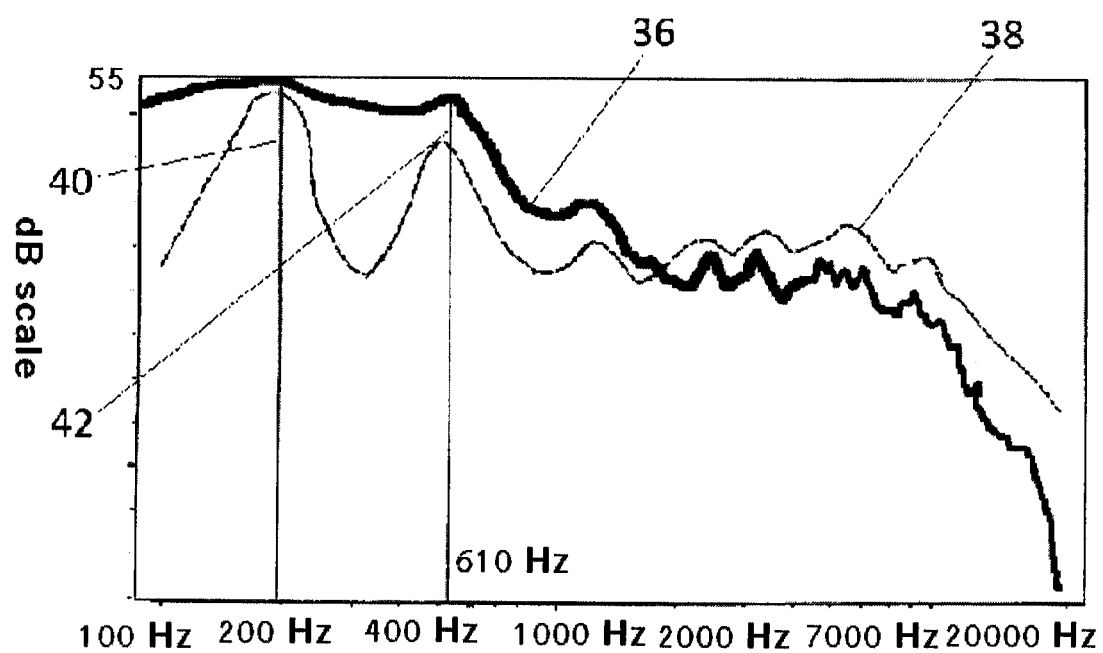
FIG. 3 displays two audio spectrograms; a stimulating audio signal spectrum and a "pure OAE" spectrogram derived from the evoked audio signal emitted by the ear(s) of a typical regular/normal person.

FIG. 3 shows two audio spectrograms; one is of a standard stimulating audio signal spectrum (36) and the other is of a typical pure OAE response (38) derived from the stimulating audio signal emitted to the ear(s) of a typical regular/normal person.

The speech stimulus heard by the ear lasts for at least the duration of one 2-3 syllables word (about 120 ms). The OAE response is captured starting 3 ms later. The Fourier transform analyses of the speech and the pure evoked OAE generate two three dimensional diagrams whose axes are: X—Time (ms) (not shown in the graph), Y—Frequency (log Hz) and Z—Amplitude (dB). For clarity the graphs at FIG. 3 show only a slice taken at time 30 ms (after about 2 syllables). The stimulus (talker) graph is indicated by 36 and the response by 38. The principal talker frequencies are indicated: 40—Lower and 42—Higher.

Since it is not practical to solve the differential equations defined by SR for each case to determine the optimal response, in order to quantify the monitored OAE response of a tested subject, her or his OAE spectrogram is compared to the OAE response spectrogram of a typical regular/normal person (such as shown in the figure). A match/deviation index serves as an indicator of quality of the pure OAE signals response.

It should be clear that the description of the embodiments and attached Figures set forth in this specification serves only for a better understanding of the invention, without limiting its scope.

It should also be clear that a person skilled in the art, after reading the present specification could make adjustments or amendments to the attached Figures and above described embodiments that would still be covered by the present invention.

The invention claims are:

1. A method for indication of abnormal sub-cognitive activity of a brainstem for the purpose of monitoring human auditory processing malfunctions, manifested by Stochastic Resonance (SR) filtering, based on evoked response signals constituting Oto-Acoustic Emissions (OAE) as measured in a human's ear, the method comprising:

stimulating the ear of people, defining a group, classified as regular, by input audio stimuli signals, for a duration of at least 120 milliseconds and frequencies in the range of 40 Hz to 12 kHz, acquiring OAE responses of said group, within said range of frequencies between 40 Hz and 12 kHz, said OAE responses being obtained along with said input audio stimuli signals, including outer hair cells (OHC) generated stochastic noise;

using a signal processor (SP) to subtract external signals so as to monitor said acquiring and collect data of said group associated with the SR-assisted filtering;

analyzing, using said SP, each OAE responses of each of said group to generate a spectrogram for each of said group, obtaining a standard set of spectrograms, stimulating, for monitoring purposes, the ear of an individual by said input audio stimuli signals, acquiring said individual's OAE responses within said range of frequencies along with said input audio stimuli signals, including said outer hair cells (OHC) generated stochastic noise;

using said SP to subtract external signals so as to monitor said acquired OAE responses of said individual associated with the SR-assisted filtering;

converting, using said SP, said individual OAE responses to an individual spectrogram, and comparing and matching between said standard set of spectrograms and said individual spectrogram, to determine malfunctioning sub-cognitive activity of said individual.

2. The method of claim 1 wherein said input audio stimuli signals are comprised of words each having at least two syllables.

3. The method of claim 1 wherein said input audio stimuli signals are comprised of words each having at least two syllables with synthetically generated stochastic noise.

4. The method of claim 1 wherein said acquiring of said OAE responses within the range of frequencies between 40 Hz and 12 kHz, is done using an OAE measurement device.

5. The method of claim 1 wherein said acquiring of said OAE responses within the range of frequencies between 40 Hz and 12 kHz, is done using a microphone.

* * * * *